US006301325B1

(12) United States Patent
Besson et al.

(10) Patent No.: US 6,301,325 B1
(45) Date of Patent: Oct. 9, 2001

(54) HALF-SCAN ALGORITHM FOR USE WITH A HIGH SPEED MULTI-ROW FAN BEAM HELICAL DETECTOR

(75) Inventors: Guy M. Besson, Wauwatosa; Tin-Su Pan, Brookfield, both of WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/470,411

(22) Filed: Dec. 22, 1999

(51) Int. Cl.[7] ........................................ A61B 6/03
(52) U.S. Cl. ........................... 378/15; 378/19; 378/901
(58) Field of Search ......................... 378/4, 15, 19, 378/901

(56) References Cited

U.S. PATENT DOCUMENTS

| | | | | |
|---|---|---|---|---|
| 5,559,847 | * | 9/1996 | Hu et al. ................................ | 378/4 |
| 5,606,585 | | 2/1997 | Hu ........................................... | 378/15 |
| 5,818,896 | | 10/1998 | Hsieh ..................................... | 378/15 |
| 5,960,056 | * | 9/1999 | Lai .......................................... | 378/4 |
| 5,991,356 | * | 11/1999 | Horiuchi et al. ...................... | 378/8 |

OTHER PUBLICATIONS

*New Classes of Helical Weighting Algorithms with Applications to Fast CT Reconstruction*, Med. Phys. 25 (8), Aug. 1998 Am. Assoc. Phys. Med, pp. 1521–1532, Guy Besson.
*Multi–slice Helical CT: Scan and Reconstruction*, Med. Phys. 26 (1), Jan. 1999 Am. Assoc. Phys. Med, pp. 1–14, Hui Hu.
*Helical CT Reconstruction with Longitudinal Filtration*, Med. Phys. 25 (11), Nov. 1998 Am. Assoc. Phys. Med, pp. 2130–2138, Hui Hu and Y. Shen.
*CT Image Reconstruction from Fan–Parallel Data*, Med. Phys. 26 (3), Aug. 1999 Am. Assoc. Phys. Med, pp. 415–426.

* cited by examiner

Primary Examiner—David V. Bruce
(74) Attorney, Agent, or Firm—Quarles & Brady, LLP; Christian G. Cabou

(57) ABSTRACT

A method and apparatus for use with a multi-row CT fan beam system for collecting data in a high speed mode and for using data corresponding to half-scans in order to generate images within one or more image planes wherein, for each beam angle corresponding to an image plane data is generated by interpolating and/or extrapolating between simultaneously collected data wherein simultaneously collected data includes data corresponding to a single source location with respect to the image plane.

22 Claims, 3 Drawing Sheets

HALF-SCAN ALGORITHM FOR USE WITH A HIGH SPEED MULTI-ROW FAN BEAM HELICAL DETECTOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to multi-slice helical computerized tomography and more particularly to an algorithm, method and apparatus for using the same which reduces the data acquisition time and data processing time required to generate an image.

In computerized tomography (CT) X-ray photon rays are directed through a patient toward a detector. Attenuated rays are detected by the detector, the amount of attenuation indicative of the make up (e.g. bone, flesh, air pocket, etc.) of the patient through which the rays traversed. The attenuation data is then processed and back-projected according to a reconstruction algorithm to generate an image of the patient's internal anatomy. Generally, the "back projection" is performed in software but, as the name implies, is akin to physically projecting rays from many different angles within an image plane through the image plane, the values of rays passing through the same image voxels being combined in some manner to have a combined effect on the voxel in the resulting image. Hereinafter the data corresponding to rays which are back projected will be referred to as back projection rays.

During data acquisition, if a patient moves, artifacts can occur in the resulting image which often render images useless or difficult to use for diagnostics purposes. For this and other reasons, as in other imaging techniques, the CT industry is constantly trying to identify ways to reduce the duration of acquisition periods without reducing the quality of the data acquired.

In addition, because huge amounts of data are acquired during an acquisition period and the processing methods for image reconstruction from the gathered data are relatively complex, a huge number of calculations are required to process data and reconstruct an image. Because of the huge number of required calculations, the time required to process collected data and reconstruct an image is appreciable. For this reason the CT industry is also constantly searching for new processing methods and algorithms which can speed up the reconstruction process.

Various CT system features and procedures have been developed to increase data acquisition speed and to speed up the reconstruction process. Some of the more popular features and procedures including fan beam acquisition, simultaneous multiple slice acquisition, helical scanning and half-scanning. In fan beam acquisition the source is collimated into a thin fan beam which is directed at a detector on a side opposite a patient. In this manner, a complete fan beam projection data set is instantaneously generated for a beam angle defined by a central ray of the source fan beam. The source and detector are rotated about an image plane to collect data from all (e.g., typically 360 degrees) beam angles. Thereafter the collected data is used to reconstruct an image in the image plane. Thus, fan beam acquisition reduces acquisition period duration.

With respect to half-scanning, assuming a patient remains still during a data acquisition period, conjugate data acquisitions (i.e., data acquired along the same path from opposite directions) should be identical. In addition, using a fan beam, at least one ray can be directed through an image plane from every possible beam angle without having to perform a complete rotation about the patient.

For example, referring to FIG. 3, an annular gantry opening 70 is illustrated with a patient slice 42 disposed (support table not illustrated) therein and with respect to a Cartesian coordinate system where the Z-axis is into the Figure and defines a transport axis. A source 10 is illustrated in first, second, third and fourth positions as 90, 90', 90" and 90''', respectively. When in the first position, source 10 generates a fan beam 40 which includes a central ray Rc and additional rays diverging therefrom along fan angles, the maximum fan angle being $\Gamma$. The beam angle B is defined as the angle formed by central ray Rc with respect to the vertical Y-axis.

When in the fourth position, source 10 generates a fan beam 40''' which also includes a central ray (not illustrated) and rays diverging therefrom to form the fan beam. By rotating the source from the first to the fourth position in a clockwise direction data is collected at least once from every possible beam angle through slice 42 (i.e., the image plane). As known in the industry, data corresponding to every beam angle corresponding to a single image plane can be collected after a $(\pi+2\Gamma)/2\pi$ rotation about the patient. Because less than an entire rotation about the image plane is required to acquire the imaging data these acquisition methods and systems are generally referred to as half-scan methods and systems. Thus, half-scan acquisition has been employed to reduce acquisition period duration in conjunction with single row detectors.

In addition, because relatively less data has to be processed in the case of half-scan imaging methods and systems to generate an image, half-scan methods and systems also have the advantage of potentially reducing data processing and reconstruction times.

While fan beams and half-scans have several advantages, often, during a diagnostics exercise a system user typically will not know the precise location within a patient of an object, cavity, etc. of interest to be imaged. For this reason, it is advantageous for a system user to be able to generate several cross sectional images in rapid succession by selecting different image/reconstruction planes. In these cases rapid data processing is extremely important to minimize delays between image generation so that a user does not lose her train of thought between image views.

Single slice detectors, fan beams and half-scans can be used to generate data in several different parallel image planes which, after data acquisition, can be used by a processor to generate an image anywhere between the image planes through interpolation/extrapolation procedures known in the art. For example, assume that during two data acquisition periods first and second data sets were acquired which correspond to first and second parallel acquisition planes, respectively, the planes separated by 0.25 inches. If a user selects an image plane for reconstructing an image which resides between the first and second acquisition planes, interpolation between data in the first and second sets can be used to estimate values of data corresponding to the selected image plane. For instance, assume that, among other rays, during the acquisition periods a first ray and a second ray were used to generate data in the first and second sets, respectively, and that the first and second rays were parallel (i.e. had the same beam and fan angles). In this case, by interpolating between the data acquired from the first and second rays generates an estimated value corresponding to a hypothetical back projection ray which is parallel to the first and second rays and which is within the image plane. By performing such interpolation to generate back projection rays for every beam and fan angle through the image plane a complete data set corresponding to the image plane is generated.

While such systems work, unfortunately, the acquisition time required to generate data corresponding to many image planes is excessive and inevitable patient movement often causes image artifacts.

One way to speed up data acquisition corresponding to several image planes is by employing a multi-row detector with a fan beam. In multi-row detector systems, a relatively thick fan beam is collimated and directed at a multi-row detector with a patient there between, each detector row in effect gathering data for a separate "slice" of the thick fan beam along the Z or translation axis perpendicular to a fan beam width. Despite each detector row having a thickness, in these systems it is assumed that the detected signals in each row correspond to a plane centered within the row as projected onto the isocenter Z. Hereinafter the central plane through a row will be referred to as a row center.

After data acquisition an interface enables a system user to select an image plane from within the area corresponding to the collected data. The selected image plane is between the row centers of at least two adjacent detector rows. After image plane selection, a processor interpolates between data corresponding to adjacent rows to generate back projection rays corresponding to the selected image plane. When another image corresponding to a different image plane is desired, after selecting the plane, the processor again identifies an acquired data subset for interpolation, additional processing and back projection. Thus, multi-row detector systems further reduce data acquisition period duration where several image planes may be selected for reconstruction.

One limitation with multi-row detectors is that, during a single acquisition period, data can only be collected which corresponds to the detector thickness. To collect additional data corresponding to a greater patient volume, after one acquisition period corresponding to a first volume, the patient has to be moved along a translation axis until a second volume which is adjacent the first volume is between the source and detector. Thereafter a second acquisition process has to be performed. Similarly, to collect additional data corresponding to a third volume the patient has to be transported to another relative location with respect to the source and detector. Required translation without acquisition necessarily prolong the acquisition period and the additional acquisition time and aligning processes inevitably result in relative discomfort, additional patient movements and undesirable image artifacts.

Helical scanning systems have been developed so that data can be collected during a single acquisition period without halting patient translation during the acquisition period. In a helical scanning system, the source and detector array are mounted on opposing surfaces of an annular gantry and are rotated there around as a patient is transported at constant speed through the gantry. The X-ray beam sweeps a helical path through the patient, hence the nomenclature "helical scanning system". Data acquisition can be sped up by increasing operating pitch (i.e., table translation speed relative to gantry rotation rate). After data is acquired the data is processed to generate back projection ray estimates and account for data nuances which are caused by the helical acquisition.

Various combinations of the fan-beam, multi-slice, half-scan and helical scanning features have been combined to realize synergies and have been somewhat successful. For example, one system combines a multi-row fan beam detector and a fan beam source with a helical scanning procedure to rapidly acquire imaging data using a high pitch/high speed mode. For example, an exemplary system including a four row detector may support a 6:1 pitch wherein the detector crosses a reconstruction plane in 0.67 rotations. It is envisioned that an eight slice scanner will be able to support an 11:1 pitch so that the detector crosses a reconstruction plane in 0.73 rotations.

Referring again to FIG. 3, in these high speed helical scanning systems, during acquisition data is acquired with source 10 at position 90, the source and detector are rotated (while data is collected) about gantry opening 70 as the patient 42 is transported there through. A processor collects data during transport and rotation from many different beam and fan angles. After source 10 rotates through a complete rotation and reaches position 90 again, additional data is gathered at that position. Because the patient 42 is transported along the Z axis during acquisition, while source 10 is at the same location 90 relative to opening 70 at the beginning and at the end of the rotation, the source and data collected are at a different Z location relative to patient 42. Hereinafter data collected for the same beam and fan angles but at different Z locations will be referred to as consecutively collected data.

Current interpolation techniques interpolate between consecutively collected data (i.e., data from source 10 at the same beam angle (e.g., position 90 in FIG. 3) and fan angle but at different Z (i.e., translation axis) locations. In other words, current interpolation techniques require data from more than a single source rotation to generate an image. In addition, because data from more than one rotation is required to interpolate, the data collection is relatively large and processing and reconstruction period durations are excessive. Moreover, because interpolation is between consecutively collected data, the resulting image has a "thickness" characteristic which corresponds to a relatively thick patient volume which is unsuitable or at least not optimal for many diagnostic purposes.

BRIEF DESCRIPTION OF THE SEVERAL VIEWS OF THE DRAWINGS

FIG. 4 is a schematic edge view illustrating a four row detector and a single image plane, the image plane illustrated in four distinct positions relative to the detector.

DETAILED DESCRIPTION OF THE INVENTION

A. Hardware

Figure 1:
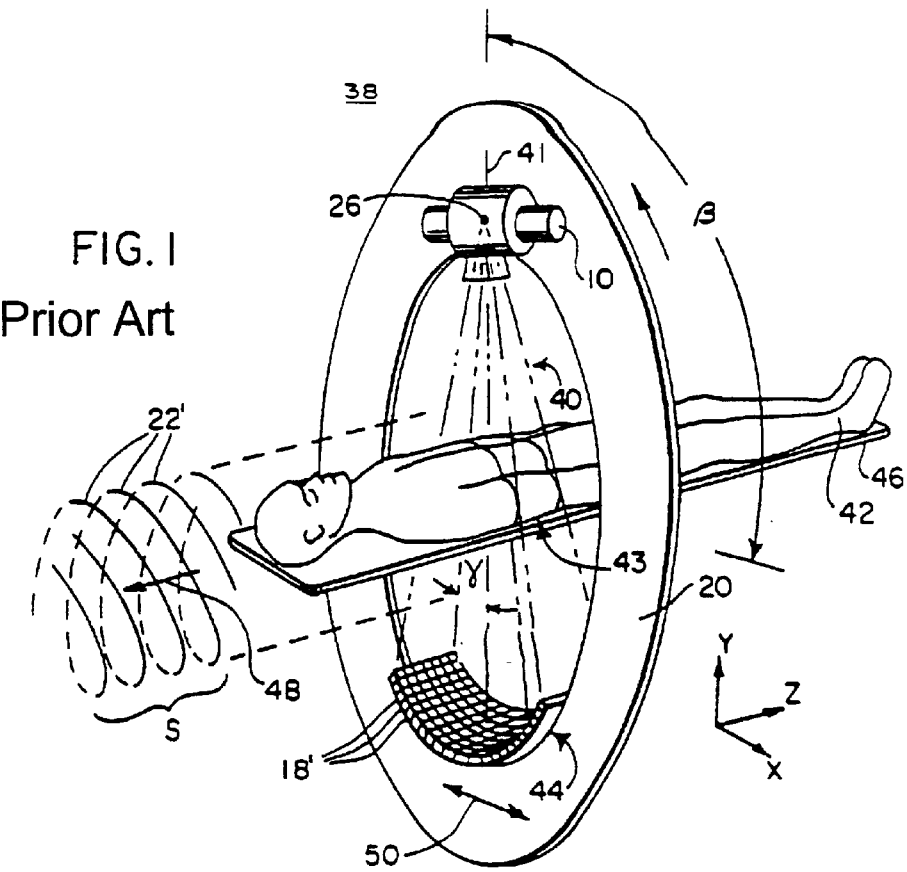
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening (70 in FIG. 3) supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by beam angle $\beta$ from an arbitrary reference position within the gantry plane 38.

A patient 42 resets on a table 46 which may be moved along a translation axis 48 aligned with the Z-axis of the Cartesian coordinate system. Table 46 crosses gantry plane 38 and is radiotranslucent so as not to interfere with the imaging process.

Figure 3:
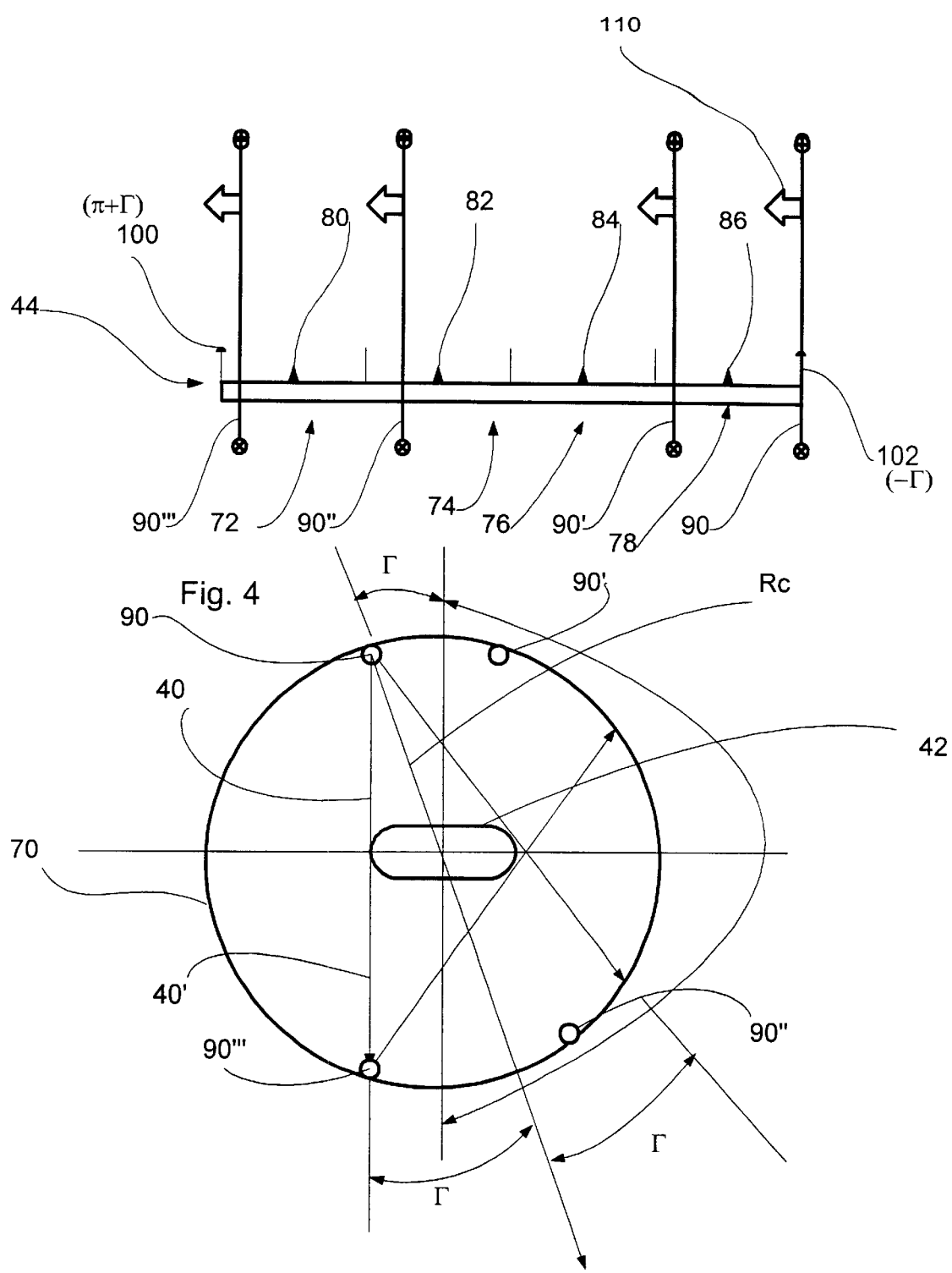
FIG. 3 is a schematic view illustrating a gantry opening with a radiation source positioned at different locations with respect to the opening and also illustrating fan beams which correspond to the beginning and end source positions of an exemplary half-scan.

The x-rays of the fan beam 40 diverge from the beam axis 41 within the gantry plane 38 across a transverse axis 50 generally orthogonal to both the beam axis 41 and the translation axis 48 at a fan beam angle $\gamma$. The x-rays of beam 40 also diverge slightly from the beam axis 41 and the gantry plane 38 across the translation axis 48. Referring also to FIG. 3, a maximum beam angle $\gamma$ is identified by symbol $\Gamma$.

After passing through patient 42, the x-rays of the fan beam 40 are received by detector array 44 which has multiple columns of detector elements 18'. The detector elements 18' are arranged in rows extending along the traverse axis 50 and columns extending along the translation axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume 43 of patient 42. In a preferred embodiment, volume 43 is greater than the slice volume measured by a conventional single slice fan beam CT system and the width of the detector array 44 is measured along its columns.

In a preferred embodiment, volume 43 is typically larger than the slice volume measured by a conventional fan beam CT system, and the width of the detector array 44 as measured along its columns is typically larger than the width of a single slice detector. The rows of detector elements 18' subdivide the fan beam detector array along the Z-axis.

Figure 2:
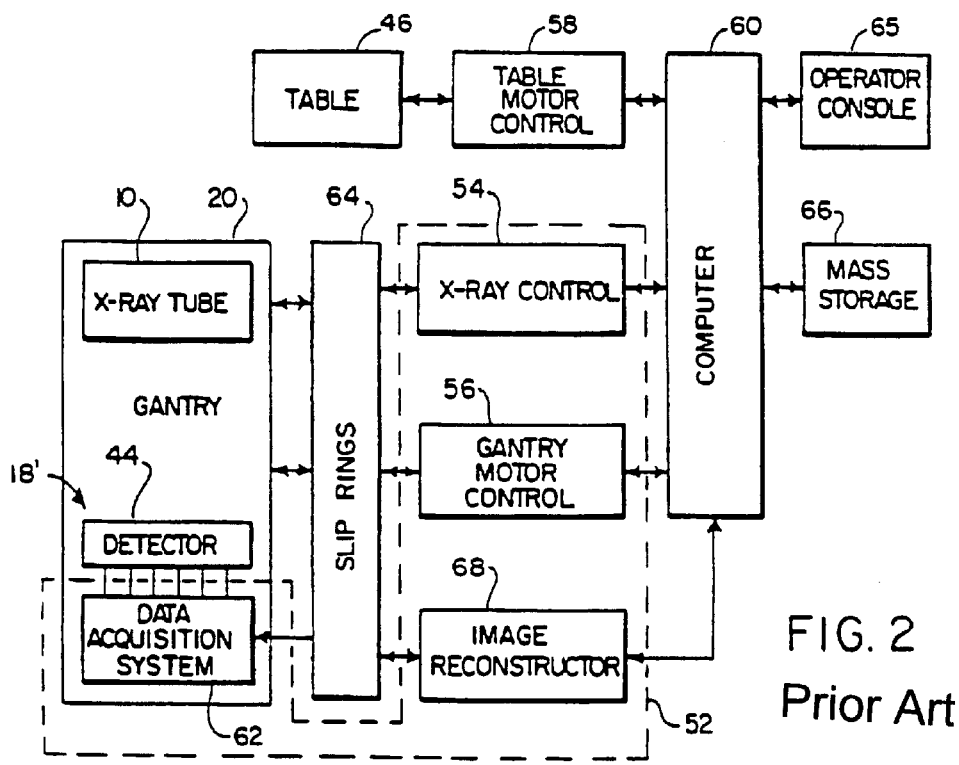
FIG. 2 is a block diagram of CT control system which may be used to control the CT apparatus of FIG. 1 and which is useful for the purposes of practicing the present invention.

Referring now to FIG. 2, an exemplary control system for controlling the CT imaging system of FIG. 1 has gantry associated control modules 52 which include an x-ray control 54, a gantry motor control 56, a data acquisition system 62 and an imagery constructor 68. The x-ray control 54 provides power and timing signals to the x-ray source 10 to turn it on and off as required under the control of a computer 60. The gantry motor control 56 controls the rotational speed and position of the gantry 20 and provides information to the computer 60 regarding gantry position. The data acquisition system 62 samples and digitizes intensity signals from the detector elements 18' of detector array 44 and the imagery constructor 68 receives the sampled and digitized intensity signals from the data acquisition system 62 each identified as to column and row of the detector element of the detector array 44, and combines the intensity signals from the detector elements 18' according to the present invention, and performs high speed imagery construction according to methods known in the art.

Each of the above modules is connected to its associated elements on the gantry 20 via slip rings 64 and serves to interface processor or computer 60 for performing various gantry functions. Slip rings 64 permit gantry 20 to rotate continuously through angles greater than 360° to acquire projection data.

The speed and position of table 46 along the translation axis 48 is communicated to and controlled by computer 60 by means of table motor control 58. In addition, computer/processor 60 runs a pulse sequencing program to perform the inventive data processing method as described in more detail below. The computer 60 receives commands and scanning parameters via operator console 65 which is generally a CRT display and keyboard. Console 65 allows an operator to enter parameters for controlling a data acquiring scan and to display the reconstructed image and other information from the computer 60. A mass storage device or memory 66 provides a means for storing operating programs for the CT imaging system, as well as image data for future reference by the operator. Both computer 60 and the image constructor have associated electronic memory (not shown) for storing data.

In operation, the gantry motor control 56 brings the gantry 20 up to a rotational speed and the table motor control begins translation of the table 46. The x-ray control 54 turns on the x-ray source 10 and projection data is acquired on the continuous basis. At each beam angle $\beta$, the projection data acquired comprises intensity signals corresponding to each detector element 18' at each particular column and row of array 44.

B. Theory

It has been recognized that, in a multi-row data acquisition system which is run at high speed (e.g., see FIGS. 1 and 2), instead of interpolating between consecutively collected data to estimate a back projection ray value within an image plane, interpolation can be performed between multi-row data generated with a source and a detector at a single location to achieve a number of advantages including reduction in acquisition period duration and reduction in data processing time after acquisition. Hereinafter, data acquired by different rows of a detector with the detector and source at a single position with respect to a gantry will be referred to as simultaneously collected data.

With respect to reducing acquisition time, interpolation between simultaneously collected data enables image reconstruction using data corresponding to a "half-scan" (e.g., less than an entire source rotation). Herein the term "half-scan" is used to refer to any scan including less than a full source rotation and may, for example, include 0.60 rotations, 0.80 rotations, 0.74 rotations and so on. A half-scan rotation requires only a fraction of the time required to perform a complete rotation and therefore acquisition time is appreciably reduced. Because acquisition period duration is reduced, likelihood of patient movement and hence image artifacts is also appreciably reduced.

With respect to reducing data processing time, the processing time is at least in part dependent upon the amount of data which must be processed to generate an image. As indicated above, with the present invention an image can be reconstructed using data corresponding to a fraction of a full rotation of the source about the patient as opposed to previous high speed helical systems which required data corresponding to more than a full source rotation about the patient. Clearly image processing time is appreciably reduced (e.g., processing time is almost halved in some cases). By reducing processing time a more user friendly interface which processes and displays images more quickly can be configured.

It has also been recognized that, in some systems which support only certain pitches or translation speeds relative to rotation speeds, the data generated during a high speed half-scan is insufficient for the purposes of image processing via interpolation of simultaneously collected data (i.e., from data collected with the source in a single location relative to the patient. To this end, the data set corresponding to a specific image plane and a specific beam angle is said to be a "complete data set" when a detector array (e.g., 44 in FIG. 1) simultaneously collects data on either side of the image plane. Similarly, the data set corresponding to a specific image plane and beam angle is said to be an "incomplete data set" when a detector array does not simultaneously collected data on either side of the image plane (i.e., for the plane and angle the array only collects data on one side of the image plane).

For example, assume that given a maximum fan beam angle $\Gamma$, data must be collected for at least 0.65 source rotation about a patient for half-scan image reconstruction, the 0.65 rotation corresponding to 0.325 rotation on either side of the image plane. Also assume that at a high speed pitch supported by the system, the width of a four row detector (where the width is between edge detector row centers) crosses the plane of reconstruction in 0.60 source rotations about a patient. In this case, for the 0.3125 through 0.325 rotation before and the 0.3125 through 0.325 rotation after the image plane, the acquisition will provide incomplete data sets (i.e., will not provide simultaneously collected data corresponding to points on both sides of the image plane) and therefore interpolation between simultaneously collected data cannot be performed. Instead, for the 0.3125 through 0.325 rotations before and after the image plane, simultaneously collected data is extrapolated to estimate back projection values.

Referring now to FIG. 4, a schematic diagram illustrating an exemplary four row detector 44 is illustrated wherein the rows extend into the Figure. The four rows are identified by numerals 72, 74, 76 and 78, respectively, and together define a thickness between detector edges 100 and 102. Detectors 72 and 78 are edge detectors because they are on the ends of detector 44. Each row 72, 74, 76 and 78 has a row center 80, 82, 84 and 86, respectively.

When data is collected by a detector row, processor 60 (see FIG. 2) assumes that the data is all collected at the corresponding row center as opposed to throughout the thickness of the row. For example, with respect to row 72, processor 60 assumes all data was collected at row center 80 and for row 74 processor 60 assumes all data was collected at row center 82 and so on. Referring to FIGS. 1 and 4, detector 44 is positioned on gantry 20 such that rows 72 through 78 are orthogonal to translation axis 48 and extend along transverse axis 50.

In some cases, prior to data acquisition, a system user will have performed some perfunctory exploratory imaging and hence will generally know the location of a desired image plane with respect to a patient's anatomy. In this case the user could limit data acquisition to a data set which includes just enough data (e.g., data corresponding to a half-scan) for reconstructing an image corresponding to the desired plane. In other cases the user may not know the exact image plane desired and therefore may want to acquire data corresponding to a patient volume (e.g., 43 in FIG. 1) from which subsets of data can be extracted for reconstructing images in specific image planes.

At this point it will be assumed that prior to acquiring imaging data, the actual plane through volume 43 which will be selected for imaging purposes is unknown. In this example, the image plane through volume 43 is selected subsequent to data acquisition via console 65 after which a specific set of the acquired data is selected for image processing. Nevertheless, for the purpose of simplifying this explanation, it will be assumed that we know the location of a specific image plane during data acquisition. This assumption enables one to easily visualize the spatial relationship between the specific image plane and relative to detectors 72 through 78.

Referring still to FIGS. 1, 3 and 4, during data acquisition, as patient 42 is transported through gantry opening 70 a patient slice corresponding to the image plane moves along the Z axis and relative to detector 44. In FIG. 4 an exemplary image plane Pi is illustrated in four separate positions with respect to detector 44, the four separate positions identified by numerals 90, 90', 90" and 90'''. The four positions 90, 90', etc., correlate to four separate snapshots in time during a single data acquisition period as detector 44 is rotated about gantry opening 70 (see also FIG. 3) and patient 42, including the patient slice corresponding to image plane Pi, is translated through opening 70. In this example, image plane positions 90, 90', 90" and 90''' in FIG. 4 correspond to like numbered source positions in FIG. 3.

Referring still to FIGS. 3 and 4, clearly during data acquisition and as the image plane Pi traverses across the detector thickness (i.e. between edges 100 and 102), during some instances and corresponding beam angles, image plane Pi is between adjacent detector row centers and during other instances and corresponding beam angles, image plane Pi is not between adjacent detector row centers. For example, on one hand, when source 10 and image plane Pi are at position 90, plane Pi is not between two detector row centers. On the other hand, at position 90' plane Pi is between row centers 84 and 86. Similarly, at position 90" plane Pi is between row centers 80 and 82 and at position 90''' plane Pi is not between adjacent row centers. Thus, for the data corresponding to positions 90' and 90", there is sufficient data for processor 60 to interpolate between adjacent detector row data to estimate back projection rays for the image plane Pi and source positions 90' and 90" (see FIG. 3) while at positions 90 and 90''' interpolation between simultaneously collected data is not possible and extrapolation is required.

Referring to FIG. 2, after imaging data required to generate an image within an image plane Pi is acquired and stored, to generate an image, processor 60 performs the interpolation and/or extrapolation processes on a half-scan data set corresponding to plane Pi generating the estimated back projection data as described above. Thereafter half-scan weights are applied to the estimated back projection data to generate weighted back projection data and the weighted data is then combined via any of several well known back projection techniques to generate an image. The half-scan weights can be derived using several different half-scan algorithms. To this end, refer to the article entitled "Optimal Short Scan Convolution for Fanbeam CT" which was authored by D. L. Parker and which was published in Med. Physics Volume 9(2) in March, 1982. Nevertheless, the invention contemplates at least one preferred algorithm wherein the half-scan weights $W_{HS}$ for scan data acquired with the source angle between 0 and $2\pi$ and centered on it are given by solving the following equation:

$$W_{HS}(\beta, \gamma) = \frac{\beta - (\pi/2) + \Gamma}{2(\Gamma - \gamma)} \quad \beta_{inf} = (\pi/2) - \Gamma \le \beta \le \beta^- \quad (1)$$
$$= (\pi/2) + \Gamma - 2\gamma$$

-continued $$W_{HS}(\beta, \gamma) = 1.0 \qquad \beta^- \leq \beta \leq \beta^+ = (3\pi/2) - \Gamma - 2\gamma$$

$$W_{HS}(\beta, \gamma) = \frac{(3\pi/2) + \Gamma - \beta}{2(\Gamma + \gamma)} \quad \beta^{\pm} \leq \beta^- \leq \beta_{sup} = (3\pi/2) + \Gamma$$

In this case a weight smoothing transformation may also be applied to the data according to the following equation:

$$f(x) = 3x^2 - 2x^3$$

with $x = W_{HS}(\beta, \gamma)$. (2)

Alternative half-scan weight algorithms are contemplated.

C. Inventive Method

Figure 5:
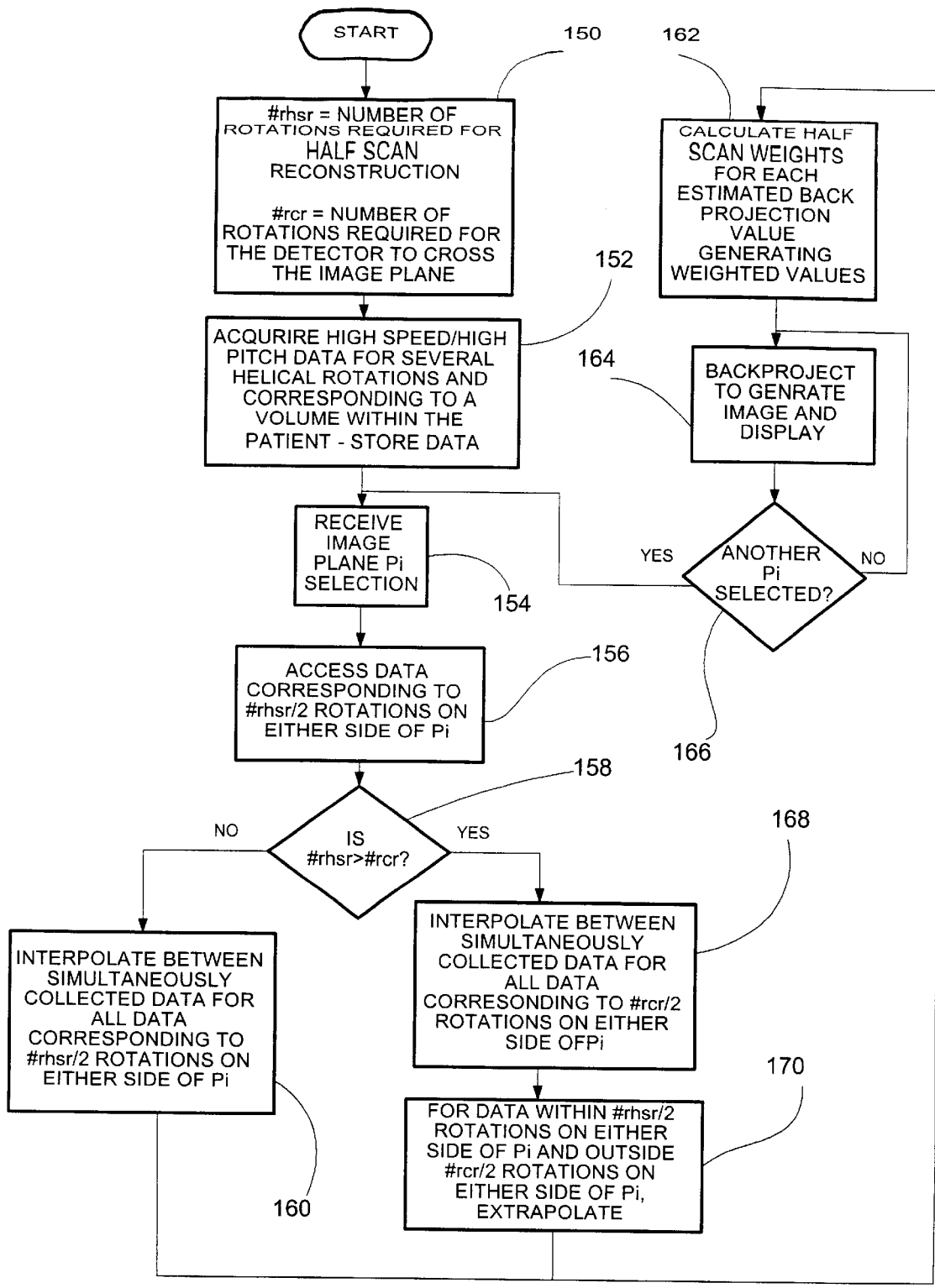
FIG. 5 is a flow chart illustrating an exemplary embodiment of the present invention.

Referring now to FIG. 5, an exemplary and preferred method according to the present invention is illustrated. Referring also to FIG. 2, at process block 150, it is assumed that processor 60 has been preprogrammed with two separate numbers including the number ($\#_{rhsr}$) of rotations required for half-scan reconstruction for the specific system configuration used with processor 60 and the number ($\#_{rcr}$) of rotations required for detector 44 to cross a single image plane given a specific pitch supported by the system. With respect to the number of rotations required for half-scan reconstruction $\#_{rhsr}$, that number is determined by solving the following equation:

$$\#_{rhsr} = (\pi + 2\Gamma)/(2\pi) \qquad (3)$$

where $\Gamma$ is the maximum fan beam angle (see FIG. 3).

Continuing, at process block 152, processor 60 controls the system of FIGS. 1 and 2 to acquire high speed/high pitch data for several helical rotations and corresponding to volume 43 of patient 42. The acquired data is stored in storage unit 66. At process block 154, a system operator uses console 65 to indicate one of a plurality of different image planes through volume 43 for which an image should be generated.

Next, at block 156 processor 60 accesses data corresponding to $\#_{rhsr}/2$ rotations (i.e., corresponding to half the data required for half-scan reconstruction of either side of the image plane Pi) on either side of the image plane Pi from mass storage unit 66. At decision block 158, processor 60 determines whether or not the number of $\#_{rhsr}$ of rotations required for half-scan reconstruction is greater than the number $\#_{rcr}$ of rotations required for the detector 44 to cross the image plane. If the number $\#_{rhsr}$ of rotations required for half-scan reconstruction is not greater than the number $\#_{rcr}$ of rotations required for the detector to cross the image plane Pi, control passes to block 160. For example, if the number of rotations required for half-scan reconstruction is 0.65 rotations and the number of rotations required for detector 44 to cross the image plane Pi is 0.73, all data required for generating an image in the specified image plane can be determined via interpolation and control passes to block 160. At block 160, processor 60 interpolates between simultaneously collected data for all data corresponding to $\#_{rhsr}/2$ rotations on either side of Pi and for each fan beam angle $\beta$ and ray angle $\gamma$. After interpolation at block 160, control passes to block 162.

Referring again to decision block 158, if the number $\#_{rhsr}$ of rotations required for half-scan reconstruction is greater than the number $\#_{rcr}$ of rotations required for the detector to cross the image plane Pi, control passes to block 168. In this case, interpolation can be used to identify data for generating an image in an image plane corresponding to certain beam angles while extrapolation must be used to generate data for forming the image from other beam angles. To this end, at process block 168 processor 60 interpolates between simultaneously collected data for all data corresponding to $\#_{rcr}/2$ rotations on either side of image plane Pi.

Then, at block 170 processor 60 extrapolates between simultaneously collected data for all data within $\#_{rhsr}/2$ rotations on either side of the image plane Pi and outside $\#_{rcr}/2$ rotations on either side of the image plane Pi. In other words, extrapolation is used to estimate projection values within the image plane only where interpolation is impossible. After extrapolation at block 170, control passes to block 162.

After the interpolation step at block 160 or the interpolation and extrapolation steps at blocks 168 and 170, at block 162 processor 160 calculates half-scan weights for each estimated backprojection value generating weighted values by solving equations 1 and 2 above. In the alternative, other half-scan weight algorithms are contemplated. After the weighted values have been generated, at block 164 processor 60 backprojects the weighted value data to generate an image and display the image on operator console 65. Until another command is received from the system operator at block 166, control continues to loop back up to block 164 and the image is displayed. At block 166, when a system operator uses console 65 to select another image plane Pi, control passes to block 154 and the process loops once again through the lower portion of FIG. 5 until an image corresponding to the newly selected image plane Pi is generated and displayed at block 164.

It should be understood that the methods and apparatuses described above are only exemplary and do not limit the scope of the invention, and that various modifications could be made by those skilled in the art that would fall under the scope of the invention. For example, as indicated above, in some cases a system will know the precise location of a desired image plane with respect to a patient's anatomy. In that case only the data required to generate an image within the desired image than would have to be acquired and the steps of selecting an image plane (i.e., 154 in FIG. 5) and selecting specific data (i.e., 156 in FIG. 5) for reconstruction would be avoided. In addition, referring again to FIG. 5, while the inventive method is described as including comparison of rotation numbers at block 158, other methods for determining if extrapolation will be used in addition to interpolation are contemplated. For example, systems which make this determination based on Z-location are contemplated.

To appraise the public of the scope of this invention, the following claims are made:

What is claimed is:

1. A method to be used with a CT system including a fan beam source and a multi-row detector, the source and detector arranged on opposite sides of a transport axis, the detector having first and second edges separated along the transport axis and having separate detector rows parallel to the edges, the source directing a fan beam including a central ray at the detector, each detector row subtended by a separate beam slice, the slices diverging from the central ray and including first and second edge slices which define beam edges orthogonal to the transport axis and which diverge from the central ray along a maximum fan angle $\Gamma$, the method for generating a cross sectional image of an object along an image plane and comprising the steps of, with the source generating the fan beam:

rotating the source and detector about the transport axis at a rotation rate;

transporting the object relative to the fan beam at a transport rate relative to the rotation rate such that the image plane traverses the first and second detector edges after a partial rotation of the source about the transport axis;

while rotating and transporting, collecting data corresponding to at least $(\pi+2\Gamma)/4\pi$ rotation and less than one half rotation on either side of the image plane; and processing the collected data to generate the cross sectional image.

2. The method of claim 1 wherein the central ray sweeps a beam angle through the object during data collection and the collected data includes complete data sets for at least a subset of beam angles, each complete data set including detector row data on both sides of the image plane and which corresponds to adjacent detector rows and wherein the step of processing includes, for each complete data set, interpolating between data in the set to generate an estimated value of a ray along the beam angle in the image plane.

3. The method of claim 2 wherein the step of interpolating includes linearly interpolating between the data corresponding to at least one detector row on either side of the image plane.

4. The method of claim 2 wherein the step of interpolating includes helically weighting the data corresponding to at least one detector row on either side of the image plane.

5. The method of claim 2 wherein the step of interpolating includes applying a sinc helical weighting to the data corresponding to all of the detector rows on each side of the image plane.

6. The method of claim 2 wherein the step of transporting includes transporting at a rate such that the fraction is at least $(\pi+2\Gamma)/2\pi$ and wherein the collected data includes a complete data set for every beam angle within the $(\pi+2\Gamma)/2\pi$ rotation.

7. The method of claim 2 wherein the step of processing further includes the step of, after interpolating, applying half-scan weights to the estimated values to generate weighted values and back-projecting the weighted values to generate the image.

8. The method of claim 7 wherein the half-scan weights are determined by solving the following equation:

$$W_{HS}(\beta, \gamma) = \frac{\beta - (\pi/2) + \Gamma}{2(\Gamma - \gamma)} \quad \beta_{inf} = (\pi/2) - \Gamma \leq \beta \leq \beta^-$$
$$= (\pi/2) + \Gamma - 2\gamma$$
$$W_{HS}(\beta, \gamma) = 1.0 \quad \beta^- \leq \beta \leq \beta^+ = (3\pi/2) - \Gamma - 2\gamma$$
$$W_{HS}(\beta, \gamma) = \frac{(3\pi/2) + \Gamma - \beta}{2(\Gamma + \gamma)} \quad \beta^\pm \leq \beta^- \leq \beta_{sup} = (3\pi/2) + \Gamma$$

and then applying the following weight smoothing transformation:

$$f(x)=3X^2-2x^3$$

where $X=W_{HS}(\beta, \gamma)$.

9. The method of claim 2 wherein the fraction is less than $(\pi+2\Gamma)/2\pi$ such that the collected data includes at least some incomplete data sets, an incomplete data set including detector row data on only one side of the image plane for a specific beam angle and wherein the step of processing further includes, for each incomplete data set, extrapolating using data in the set to generate an estimated value of a ray along the beam angle in the image plane.

10. The method of claim 9 wherein the step of processing further includes the step of, after interpolating, applying half-scan weights to the estimated values to generate weighted values and back-projecting the weighted values to generate the image.

11. The method of claim 10 wherein the half-scan weights are determined by solving the following equation:

$$W_{HS}(\beta, \gamma) = \frac{\beta - (\pi/2) + \Gamma}{2(\Gamma - \gamma)} \quad \beta_{inf} = (\pi/2) - \Gamma \leq \beta \leq \beta^-$$
$$= (\pi/2) + \Gamma - 2\gamma$$
$$W_{HS}(\beta, \gamma) = 1.0 \quad \beta^- \leq \beta \leq \beta^+ = (3\pi/2) - \Gamma - 2\gamma$$
$$W_{HS}(\beta, \gamma) = \frac{(3\pi/2) + \Gamma - \beta}{2(\Gamma + \gamma)} \quad \beta^\pm \leq \beta^- \leq \beta_{sup} = (3\pi/2) + \Gamma$$

and then applying the following weight smoothing transformation:

$$f(x)=3x^2-2x^3$$

where $x=W_{HS}(\beta, \gamma)$.

12. An apparatus for use with a CT system including a fan beam source and a multi-row detector, the source and detector arranged on opposite sides of a transport axis, the detector having first and second edges separated along the transport axis and having separate detector rows parallel to the edges, the source directing a fan beam including a central ray at the detector, each detector row subtended by a separate beam slice, the slices diverging from the central ray and including first and second edge slices which define beam edges orthogonal to the transport axis and which diverge from the central ray along a maximum fan angle $\Gamma$, the apparatus for generating a cross sectional image of an object along an image plane and comprising, with the source generating the fan beam:

a processor running a pulse sequencing program to perform the steps of:

rotating the source and detector about the transport axis at a rotation rate;

transporting the object relative to the fan beam at a transport rate relative to the rotation rate such that the image plane traverses the first and second detector edges after a partial rotation of the source about the transport axis;

while rotating and transporting, collecting data corresponding to at least $(\pi+2\Gamma)/4\pi$ rotation and less than one half rotation on either side of the image plane; and processing the collected data to generate the cross sectional image.

13. The apparatus of claim 12 wherein the central ray sweeps a beam angle through the object during data collection and the collected data includes complete data sets for at least a subset of beam angles, each complete data set including detector row data on both sides of the image plane and which corresponds to adjacent detector rows and wherein the processor runs the program to perform the step of processing by, for each complete data set, interpolating between data in the set to generate an estimated value of a ray along the beam angle in the image plane.

14. The apparatus of claim 13 wherein the processor runs the program to perform the step of interpolating by linearly interpolating between the data corresponding to at least one detector row on either side of the image plane.

15. The apparatus of claim 13 wherein the processor runs the program to perform the step of interpolating by helically weighting the data corresponding to at least one detector row on either side of the image plane.

16. The apparatus of claim 13 wherein the processor runs the program to perform the step of interpolating by applying a modified sinc helical weighting to the data corresponding to all of the detector rows on each side of the image plane.

17. The apparatus of claim 13 wherein the processor runs the program to perform the step of transporting by transporting at a rate such that the fraction is at least $(\pi+2\Gamma)/2\pi)$ and wherein the collected data includes a complete data set for every beam angle within the $(\pi+2\Gamma)/2\pi)$ rotation.

18. The apparatus of claim 13 wherein the processor further runs the program to perform the step of, after interpolating, applying half-scan weights to the estimated values to generate weighted values and back-projecting the weighted values to generate the image.

19. The apparatus of claim 18 wherein the half-scan weights are determined by solving the following equation:

$$W_{HS}(\beta, \gamma) = \frac{\beta - (\pi/2) + \Gamma}{2(\Gamma - \gamma)} \quad \beta_{inf} = (\pi/2) - \Gamma \leq \beta \leq \beta^-$$
$$= (\pi/2) + \Gamma - 2\gamma$$
$$W_{HS}(\beta, \gamma) = 1.0 \quad \beta^- \leq \beta \leq \beta^+ = (3\pi/2) - \Gamma - 2\gamma$$
$$W_{HS}(\beta, \gamma) = \frac{(3\pi/2) + \Gamma - \beta}{2(\Gamma + \gamma)} \quad \beta^\pm \leq \beta^- \leq \beta_{sup} = (3\pi/2) + \Gamma$$

and then applying the following weight smoothing transformation:

$$f(x)=3x^2-2x^3$$

where $x=W_{HS}(\beta, \gamma)$.

20. The apparatus of claim 13 wherein the fraction is less than $(\pi+2\Gamma)/2\pi)$ such that the collected data includes at least some incomplete data sets, an incomplete data set including detector row data on only one side of the image plane for a specific beam angle and wherein the processor runs the program to perform the step of processing by, also, for each incomplete data set, extrapolating using data in the set to generate an estimated value of a ray along the beam angle in the image plane.

21. The apparatus of claim 20 wherein the processor runs the program to perform the step of processing by, also, after interpolating, applying half-scan weights to the estimated values to generate weighted values and back-projecting the weighted values to generate the image.

22. The apparatus of claim 21 wherein the half-scan weights are determined by solving the following equation:

$$W_{HS}(\beta, \gamma) = \frac{\beta - (\pi/2) + \Gamma}{2(\Gamma - \gamma)} \quad \beta_{inf} = (\pi/2) - \Gamma \leq \beta \leq \beta^-$$
$$= (\pi/2) + \Gamma - 2\gamma$$
$$W_{HS}(\beta, \gamma) = 1.0 \quad \beta^- \leq \beta \leq \beta^+ = (3\pi/2) - \Gamma - 2\gamma$$
$$W_{HS}(\beta, \gamma) = \frac{(3\pi/2) + \Gamma - \beta}{2(\Gamma + \gamma)} \quad \beta^\pm \leq \beta^- \leq \beta_{sup} = (3\pi/2) + \Gamma$$

and then applying the following weight smoothing transformation:

$$f(x)=3x^2-2x^3$$

where $x=W_{HS}(\beta, \gamma)$.

* * * * *